US012635876B2

(12) United States Patent
Farsiu et al.

(10) Patent No.: US 12,635,876 B2
(45) Date of Patent: May 26, 2026

---

(54) RAPID MULTI-CHANNEL ADAPTIVE OPTICS SCANNING LIGHT OPHTHALMOSCOPY

(71) Applicant: Duke University, Durham, NC (US)

(72) Inventors: Sina Farsiu, Durham, NC (US); Joseph Izatt, Durham, NC (US); Jongwan Park, Durham, NC (US); Kristen Hagan, Durham, NC (US); Ryan McNabb, Durham, NC (US); Theodore DuBose, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 283 days.

(21) Appl. No.: 18/587,173

(22) Filed: Feb. 26, 2024

(65) Prior Publication Data

US 2024/0423468 A1 Dec. 26, 2024

Related U.S. Application Data

(60) Provisional application No. 63/448,392, filed on Feb. 27, 2023.

(51) Int. Cl.
 *A61B 3/10* (2006.01)
 *A61B 3/02* (2006.01)
 (Continued)

(52) U.S. Cl.
 CPC .............. *A61B 3/12* (2013.01); *A61B 3/1015* (2013.01); *A61B 3/14* (2013.01); *G06T 7/0014* (2013.01); *G06T 2207/30041* (2013.01)

(58) Field of Classification Search
 CPC ......... A61B 3/02; A61B 3/102; A61B 3/1025; A61B 3/113; A61B 3/1015; A61B 3/103; A61B 3/1005; A61B 3/1225; A61B 3/024
 (Continued)

(56) References Cited

U.S. PATENT DOCUMENTS 6,890,076 B2 5/2005 Roorda
7,284,862 B1 10/2007 Lai et al.
(Continued)

FOREIGN PATENT DOCUMENTS

JP 5635898 B2 12/2014

OTHER PUBLICATIONS

Roorda, Austin, et al., "Adaptive optics scanning laser ophthalmoscopy," Optics Express, May 6, 2002, pp. 405-412, vol. 10, issue 9.
(Continued)

*Primary Examiner* — Dawayne Pinkney
(74) *Attorney, Agent, or Firm* — Talem IP Law, LLP

(57) ABSTRACT

A system includes a reflective mask positioned in a first plane, a digital micromirror device (DMD) that is positioned in a second plane to receive transmitted light from the reflective mask via a non-confocal channel. The DMD includes micromirrors that rotate between an ON state and an OFF state. The system further includes an ON image detector that captures ON image data of the transmitted light directed by the micromirrors in the ON state and an OFF image detector that captures OFF image data of the transmitted light directed by the micromirrors in the OFF state. A method of image reconstruction includes using the captured data to compare against artificial image data created by a machine learning model/reconstruction network and iteratively updating weights (e.g., of the machine learning model/reconstruction network) for generating an artificial image from the artificial image data until a minimum threshold is reached.

19 Claims, 10 Drawing Sheets

(51) Int. Cl.
     *A61B 3/12*      (2006.01)
     *A61B 3/14*      (2006.01)
     *G06T 7/00*      (2017.01)
(58) Field of Classification Search
     USPC ........ 351/206, 200, 205, 209–212, 221–223,
                                                              351/246
     See application file for complete search history.

(56)                    References Cited

U.S. PATENT DOCUMENTS

| | | |
|---|---|---|
| 7,404,640 B2 | 7/2008 | Ferguson et al. |
| 7,896,496 B2 | 3/2011 | Hammer et al. |
| 8,201,943 B2 | 6/2012 | Hammer et al. |
| 9,740,003 B2 | 8/2017 | Potsaid et al. |
| 9,918,631 B2 | 3/2018 | Saito |
| 9,924,862 B2 | 3/2018 | Brown et al. |
| 2012/0154747 A1 | 6/2012 | Makihira |

OTHER PUBLICATIONS

Dubra, Alfredo, et al., "Noninvasive imaging of the human rod photoreceptor mosaic using a confocal adaptive optics scanning ophthalmoscope," Biomedical Optics Express, Jul. 1, 2011 (accessible: Jun. 8, 2011), pp. 1864-1876, vol. 2, issue 7.

Rossi, Ethan A., et al., "Imaging individual neurons in the retinal ganglion cell layer of the living eye," Proceedings of the National Academy of Sciences, Jan. 17, 2017 (accessible: Jan. 3, 2017), pp. 586-591, vol. 114, issue 3.

Gofas-Salas, Elena, et al., "Design of a radial multi-offset detection pattern for in vivo phase contrast imaging of the inner retina in humans," Biomedical Optics Express, Jan. 1, 2022 (available: Dec. 6, 2021), pp. 117-132, vol. 13, issue 1.

Boretsky, Adam et al., "In vivo imaging of photoreceptor disruption associated with age-related macular degeneration: A pilot study," Lasers in Surgery and Medicine, Oct. 2012, 17 pages, vol. 44, issue 8.

Curcio, C. A., et al., "Photoreceptor loss in age-related macular degeneration," Investigative Ophthalmology & Visual Science, Jun. 1996, pp. 1236-1249, vol. 37, issue 7.

Gao, Jiangang, et al., "Progressive photoreceptor degeneration, outer segment dysplasia, and rhodopsin mislocalization in mice with targeted disruption of the retinitis pigmentosa-1 ( Rp1 ) gene," Proceedings of the National Academy of Sciences, Apr. 16, 2002, pp. 5698-5703, vol. 99, issue 8.

Kolb, H., et al., "Electron microscopic observations of human retinitis pigmentosa, dominantly inherited," Investigative Ophthalmology, Jul. 1974, pp. 487-498, vol. 13, issue 7.

Sun, Lynn W., et al., "Assessing Photoreceptor Structure in Retinitis Pigmentosa and Usher Syndrome," Investigative Opthalmology Visual Science, May 4, 2016, pp. 2428-2442, vol. 57, issue 6.

Litts, Katie M., et al., "Photoreceptor-Based Biomarkers in AOSLO Retinal Imaging," Investigative Opthalmology Visual Science, Sep. 5, 2017, p. BIO255-67, vol. 58, issue 6.

Sulai, Yusufu N., et al., "Visualization of retinal vascular structure and perfusion with a nonconfocal adaptive optics scanning light ophthalmoscope," Journal of the Optical Society of America A, Mar. 1, 2014, 21 pages, vol. 31, issue 3.

Wynne, Niamh, et al., "Promises and pitfalls of evaluating photoreceptor-based retinal disease with adaptive optics scanning light ophthalmoscopy (AOSLO)," Progress in Retinal and Eye Research, Jul. 2021 (available: Nov. 6, 2020), 75 pages, vol. 83, article 100920.

Dubra, Alfredo, et al., "Reflective afocal broadband adaptive optics scanning ophthalmoscope," Biomedical Optics Express, Jun. 1, 2011 (accessible May 27, 2011), pp. 1757-1768, vol. 2, issue 6.

Scoles, Drew, et al., "In Vivo Imaging of Human Cone Photoreceptor Inner Segments," Investigative Opthalmology Visual Science, Jul. 11, 2014, pp. 4244-4251, vol. 55, issue 7.

Mozaffari, Sanam, et al., "Versatile multi-detector scheme for adaptive optics scanning laser ophthalmoscopy," Biomedical Optics Express, Nov. 1, 2018 (accessible Oct. 16, 2018), pp. 5477-5488, vol. 9, issue 11.

Sapoznik, Kaitlyn A., et al., "Enhanced retinal vasculature imaging with a rapidly configurable aperture," Biomedical Optics Express, Mar. 1, 2018 (accessible Feb. 23, 2018), pp. 1323-1333, vol. 9, issue 3.

Chui, Toco Y. P., et al., "The use of forward scatter to improve retinal vascular imaging with an adaptive optics scanning laser ophthalmoscope," Biomedical Optics Express, Oct. 1, 2012 (accessible Sep. 13, 2012), pp. 2537-2549, vol. 3, issue 10.

Guevara-Torres, A., et al., "Origin of cell contrast in offset aperture adaptive optics ophthalmoscopy," Optics Letters, Feb. 6, 2020, 12 pages, vol. 45, issue 4.

Cunefare, David, et al., "Deep learning based detection of cone photoreceptors with multimodal adaptive optics scanning light ophthalmoscope images of achromatopsia," Biomedical Optics Express, Aug. 1, 2018 (accessible: Jul. 18, 2018), pp. 3740-3756, vol. 9, issue 8.

Cunefare, David, et al., "RAC-CNN: multimodal deep learning based automatic detection and classification of rod and cone photoreceptors in adaptive optics scanning light ophthalmoscope images," Biomedical Optics Express, Aug. 1, 2019 (accessible Jul. 8, 2019), pp. 3815-3832, vol. 10, issue 8.

Baraniuk, Richard, "Compressive Sensing [Lecture Notes]," IEEE Signal Processing Magazine, Jul. 2007, 9 pages, vol. 24, issue 4.

Ulyanov, Dmitry, et al., "Deep Image Prior," International Journal of Computer Vision, Jul. 2020 (accessible May 17, 2020), 23 pages, vol. 128, issue 7.

Dubra, Alfredo, et al., "Registration of 2D Images from Fast Scanning Ophthalmic Instruments," Biomedical Image Registration, Lecture Notes in Computer Science 2010, pp. 60-71, vol. 6204, Springer Berlin Heidelberg.

Cunefare, David, et al., "Open source software for automatic detection of cone photoreceptors in adaptive optics ophthalmoscopy using convolutional neural networks," Scientific Reports, Jul. 26, 2017, pp. 1-11, vol. 7, issue 1, article 6620.

Merino, David, et al., "Adaptive optics scanning laser ophthalmoscope imaging: technology update," Clinical Ophthalmology, Apr. 26, 2016, pp. 743-755, vol. 10, issue 2016.

Fischer, Jorg, et al., "Scanning Laser Ophthalmoscopy (SLO)," High Resolution Imaging in Microscopy and Ophthalmology, Aug. 14, 2019, pp. 35-57, Springer International Publishing.

Fei, Xiao, et al., "Deblurring adaptive optics retinal images using deep convolutional neural networks," Biomedical Optics Express, Dec. 1, 2017 (Accessible: Nov. 16, 2017), pp. 5675-5687, vol. 8, issue 12.

Young, Laura K., et al., "Compact, modular and in-plane AOSLO for high-resolution retinal imaging," Biomedical Optics Express, Sep. 1, 2018 (Accessible: Aug. 15, 2018), pp. 4275-4293, vol. 9, issue 9.

Chen, Hao, et al., "Automatic Dewarping of Retina Images in Adaptive Optics Confocal Scanning Laser Ophthalmoscope," IEEE Access, May 3, 2019, pp. 59585-59599, vol. 7.

Li, Wanyue, et al., "Quality improvement of adaptive optics retinal images using conditional adversarial networks," Biomedical Optics Express, Feb. 1, 2020 (Accessible: Jan. 14, 2020), pp. 831-849, vol. 11, issue 2.

Liu, Shudong, et al., "Deep-Learning Image Stabilization for Adaptive Optics Ophthalmoscopy," Information, Nov. 8, 2022, pp. 1-16, vol. 13, issue 11, article 531.

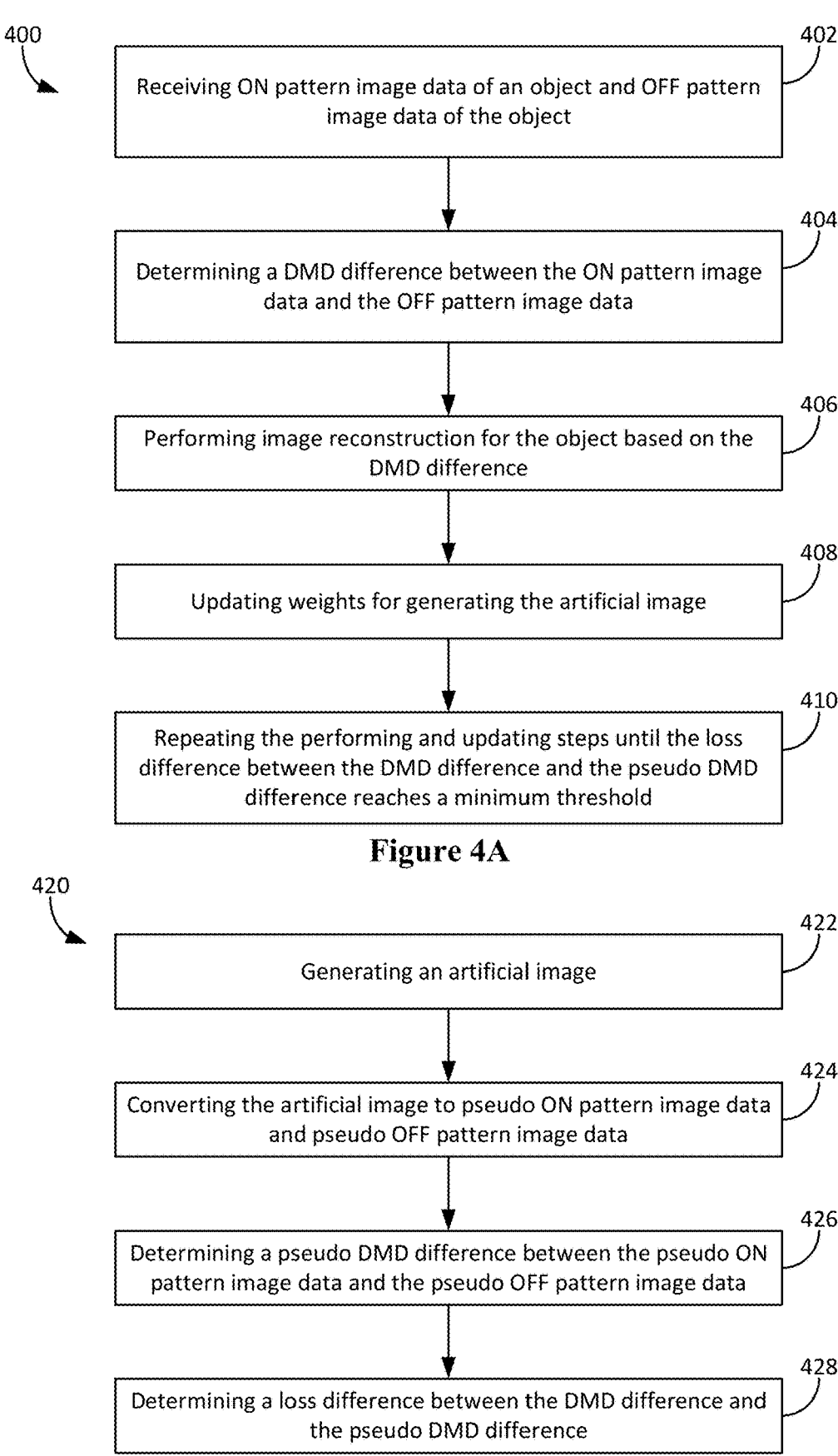

400

402

Receiving ON pattern image data of an object and OFF pattern image data of the object

404

Determining a DMD difference between the ON pattern image data and the OFF pattern image data

406

Performing image reconstruction for the object based on the DMD difference

408

Updating weights for generating the artificial image

410

Repeating the performing and updating steps until the loss difference between the DMD difference and the pseudo DMD difference reaches a minimum threshold

Generating an artificial image

424

Converting the artificial image to pseudo ON pattern image data and pseudo OFF pattern image data

426

Determining a pseudo DMD difference between the pseudo ON pattern image data and the pseudo OFF pattern image data

428

Determining a loss difference between the DMD difference and the pseudo DMD difference

Figure 4B

RAPID MULTI-CHANNEL ADAPTIVE OPTICS SCANNING LIGHT OPHTHALMOSCOPY

CROSS-REFERENCE TO RELATED APPLICATIONS

This application claims the benefit of U.S. Provisional Application Ser. No. 63/448,392, filed Feb. 27, 2023.

STATEMENT REGARDING FEDERALLY SPONSORED RESEARCH

This invention was made with Government support under Federal Grant no. CBET-1902904 awarded by the National Science Foundation. The Federal Government has certain rights to this invention.

BACKGROUND

Adaptive optics scanning light ophthalmoscopy (AO-SLO) is the most common imaging technology for in vivo imaging of individual retinal cells. Recently, non-confocal AOSLO modalities have been introduced to provide an alternative of information to confocal AOSLO. These non-confocal AOSLO modalities detect multiply-scattered, non-confocal light by displacing the detection channel from its on-axis location. Two main approaches for non-confocal AOSLO are multi-detector imaging and multi-offset aperture imaging, whose ability to capture 2-D non-confocal light intensity information via multi-channel detection has allowed for enhanced visualization of diverse retinal structures, including vessels, retinal ganglion cells, and immune cells. However, multi-detector imaging requires an array of expensive high-speed, high-sensitive detectors, such as photomultiplier tubes (PMTs), which greatly increases system complexity and cost. Multi-offset aperture imaging serially acquires individual channel images by moving a single detection channel, thus increasing imaging duration and increasing susceptibility to motion. These limitations have prevented non-confocal AOSLO from being utilized in clinical practice. Accordingly, an AOSLO system with an adequate number of non-confocal channels to accurately image retinal structures and that has increased imaging speed without the relatively expensive optical components used in previously disclosed non-confocal AOSLO modalities is desirable.

BRIEF SUMMARY

Systems and techniques for rapid deep-compressed multi-channel adaptive optics scanning light ophthalmoscopy (DCAOSLO) are described herein. Advantageously, the described systems and methods provide an adequate number of non-confocal channels to accurately image retinal structures fast without the relatively expensive optical components used in previously disclosed non-confocal AOSLO modalities, resulting in systems and methods that can feasibly be adopted in clinical practice.

A system includes a reflective mask positioned in a first plane, a digital micromirror device (DMD) that is positioned in a second plane to receive transmitted light from the reflective mask via a non-confocal channel. The DMD includes micromirrors that rotate between an ON state and an OFF state. The system further includes an ON image detector that captures ON image data of the transmitted light directed by the micromirrors in the ON state and an OFF image detector that captures OFF image data of the transmitted light directed by the micromirrors in the OFF state.

In some cases, the DMD further includes a DMD controller and memory storing instructions that when executed by the DMD controller, direct the DMD to rotate the micromirrors between the ON state and the OFF according to a pre-stored DMD pattern sequence during imaging. In some cases, the non-confocal channel is a plurality of non-confocal channels. In some cases, the micromirrors of the DMD are divided into distinct sections corresponding to the pre-stored DMD pattern sequence. In some cases, the DMD is further positioned to receive the transmitted light from the reflective mask via a confocal channel. In some cases, each distinct section receives the transmitted light from a different non-confocal channel or a confocal channel. In some cases, the instructions executed by the DMD controller further direct the DMD to repeatedly cycle through the pre-stored DMD pattern sequence in response to TTL pulses generated from a horizontal scanner. In some cases, the instructions executed by the DMD controller further direct the DMD to tag a first cycle of the pre-stored DMD pattern sequence for identification.

In some cases, the ON state is +12 degrees relative to the second plane and the OFF state is −12 degrees relative to the second plane. In some cases, the system further includes an ON lens positioned between the DMD and the ON image detector and an OFF lens positioned between the DMD and the OFF image detector. In some cases, the ON image detector and the OFF image detector are photomultiplier tubes. In some cases, the ON image detector and the OFF image detector are avalanche photodiodes. In some cases, the reflective mask is a reflective elliptical annular mask. In some cases, the reflective mask is a reflective pinhole mask.

In some cases, the system further includes a third light detector that captures confocal image data from reflected light that is reflected from the reflective mask via a confocal channel and a pinhole positioned between the third light detector and the reflective mask. In some cases, the system further includes a light source of the light for imaging, a wavefront sensing beacon arranged to provide additional light, a wavefront sensor arranged to receive the light, a first dichroic arranged to combine light from the light source with the additional light from the wavefront sensing beacon, a second dichroic arranged to reflect the light to the reflective mask and to transmit the additional light from the wavefront sensing beacon and positioned between the first dichroic and the wavefront sensor, four concave spherical mirror telescopes arranged in a non-planar folding configuration and positioned between the beam splitter and an object to be imaged, a horizontal scanner, a vertical scanner, and a deformable mirror positioned within the four concave spherical mirror telescopes. In some cases, the system further includes a system controller and memory storing instructions that when executed by the system controller, direct the system to adjust the horizontal scanner, the vertical scanner, and the deformable mirror positioned within the four concave spherical mirror telescopes to image the object.

A method of image reconstruction includes receiving ON pattern image data of an object and OFF pattern image data of the object. The ON pattern image data is captured by an ON image detector that receives light from micromirrors of a digital micromirror device (DMD) that are rotated to an ON state according to a pre-stored DMD pattern sequence and the OFF pattern image data is captured by an OFF image detector that receives light from micromirrors of the DMD that are rotated to an OFF state according to the pre-stored DMD pattern sequence. The method further includes determining a DMD difference between the ON pattern image data and the OFF pattern image data and performing image reconstruction for the object based on the DMD difference. The image reconstruction includes generating an artificial image, converting the artificial image to pseudo ON pattern image data and pseudo OFF pattern image data, determining a pseudo DMD difference between the pseudo ON pattern image data and the pseudo OFF pattern image data, and determining a loss difference between the DMD difference and the pseudo DMD difference. The method further includes updating weights (e.g., of a machine learning model/reconstruction network) for generating the artificial image and repeating the performing and updating steps until the loss difference between the DMD difference and the pseudo DMD difference reaches a minimum threshold.

In some cases, the micromirrors of the DMD are divided into distinct sections corresponding to the pre-stored DMD pattern sequence and each distinct section receives the transmitted light from a different non-confocal channel or a confocal channel. In some cases, the method further includes summing the ON pattern image data and the OFF pattern image data. A set of inputs to the reconstruction network for generating the artificial image includes the sum of the ON image data and the OFF image data. In some cases, a machine learning model and/or reconstruction network performs the step of generating the artificial image. In some cases, updating the weights (e.g., of the machine learning model/reconstruction network) for generating the artificial image includes minimizing a mean squared error for the determined loss difference between the DMD difference and the pseudo DMD difference. In some cases, the method further includes displaying a final artificial image upon reaching the minimum threshold.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 4A illustrates a flow diagram of a method of creating a reconstruction image from image data collected using a multi-channel device as described herein.

FIG. 4B illustrates a flow diagram of a method of performing image reconstruction that can be used as part of a method of creating a reconstruction image.

DETAILED DESCRIPTION

Systems and techniques for rapid deep-compressed multi-channel adaptive optics scanning light ophthalmoscopy (DCAOSLO) are described herein. Advantageously, the described systems and methods provide an adequate number of non-confocal channels to accurately image retinal structures fast without the relatively expensive optical components used in previously disclosed non-confocal AOSLO modalities, resulting in systems and methods that can feasibly be adopted in clinical practice.

DCAOSLO achieves efficient multi-channel detection of light via compressed sensing. Compressed sensing allows for the reconstruction of a high-dimensional signal from only a few compressed or random measurements. Compressed sensing on returning light is performed by displaying pre-designed binary random patterns on a digital micromirror device positioned in a de-scanned (retinal) conjugate plane. Although this application is described in the context of AOSLO imaging, the systems and methods described herein can be used in other imaging systems that require multi-channel light detection in a scanning microscope, such as for example, hyperspectral microscopy, non-AOSLO (e.g., without AO components), and computational AOSLO (without wavefront sensing beacon(s) and/or wavefront sensor(s).

Figure 1A:
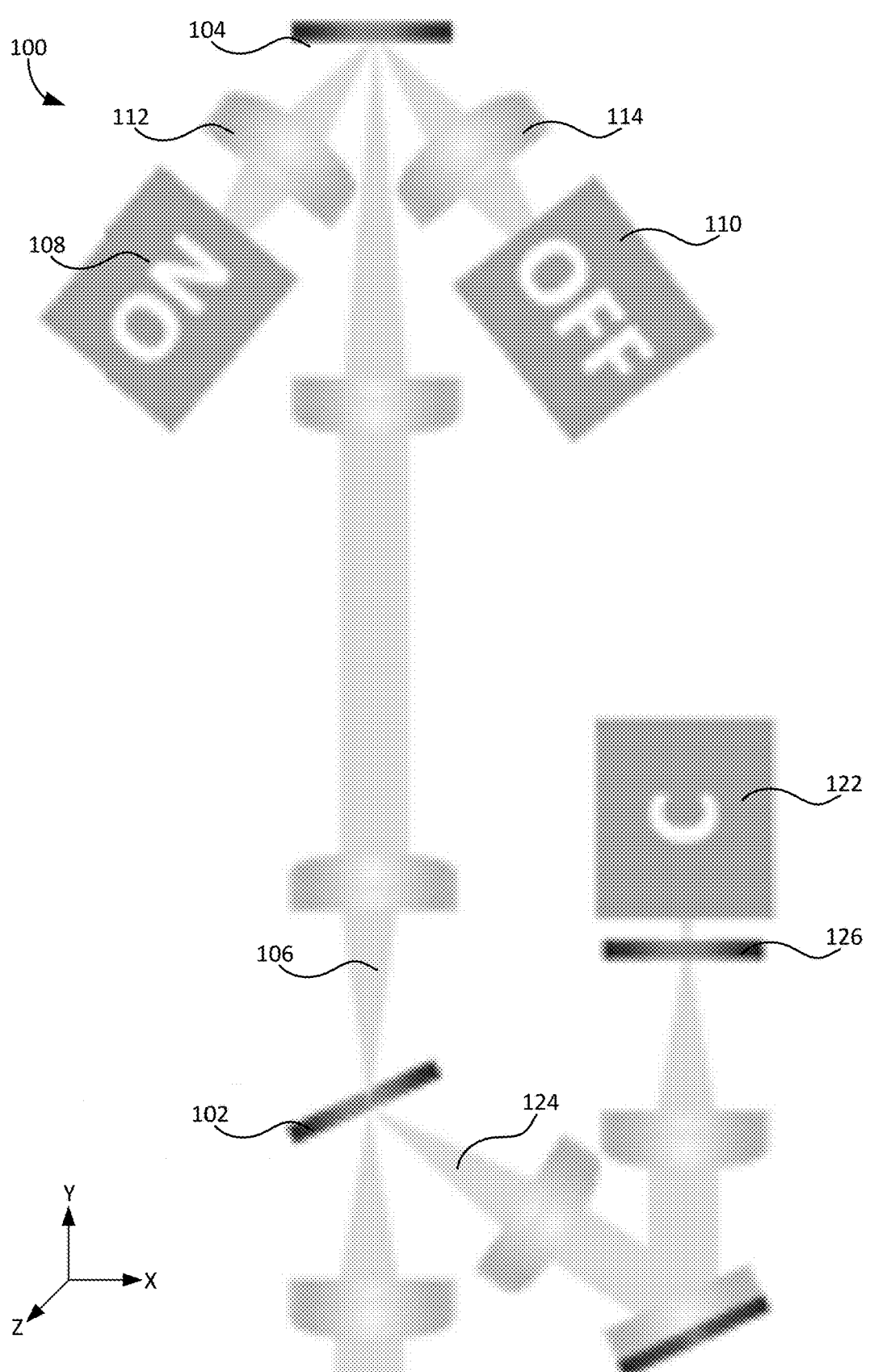
FIG. 1A illustrates a multi-channel device that can be used as a detector in a DCAOSLO system.

FIG. 1A illustrates a multi-channel device that can be used as a detector in a DCAOSLO system. Referring to FIG. 1A, a multi-channel device 100 includes a reflective mask 102 positioned in a first plane (e.g., X-plane) and a digital micromirror device (DMD) 104 that is positioned in a second plane (e.g., Y-plane) to receive transmitted light 106 from the reflective mask 102 via one or more non-confocal channels. The DMD 104 includes micromirrors that rotate between an ON state and an OFF state and a DMD controller (not shown). The multi-channel device 100 further includes an ON image detector 108 that captures ON image data of the transmitted light 106 directed by the micromirrors in the ON state and an OFF image detector 110 that captures OFF image data of the transmitted light 106 directed by the micromirrors in the OFF state. The collected image data is able to be used to create a reconstruction image using the method 400 described with respect to FIG. 4A.

It should be understood that the X-plane and Y-plane are merely used for exemplary purposes and may be orientated in any way to transmit and/or reflect light in a DCAOSLO system.

In some cases, the ON state is +12 degrees relative to the second plane and the OFF state is −12 degrees relative to the second plane. In some cases, the system further includes an ON lens 112 positioned between the DMD 104 and the ON image detector 108 and an OFF lens 114 positioned between the DMD 104 and the OFF image detector 110. In some cases, the ON image detector 108 and the OFF image detector 110 are photomultiplier tubes. In some cases, the ON image detector 108 and the OFF image detector 110 are avalanche photodiodes. In some cases, the reflective mask 102 is a reflective elliptical annular mask. In some cases, the reflective mask 102 is a reflective pinhole mask. In some cases (e.g., AOSLO specific cases), the multi-channel device 100 further includes a third light detector 122 that captures confocal image data from reflected light 124 that is reflected from the reflective mask 102 via a confocal channel and a pinhole 126 positioned between the third light detector 122 and the reflective mask 102. In some cases, the multi-channel device 100 further includes a third light detector 122 that captures darkfield non-confocal image data from reflected light 124 that is reflected from the reflective mask 102 via a non-confocal channel.

Figure 1B:
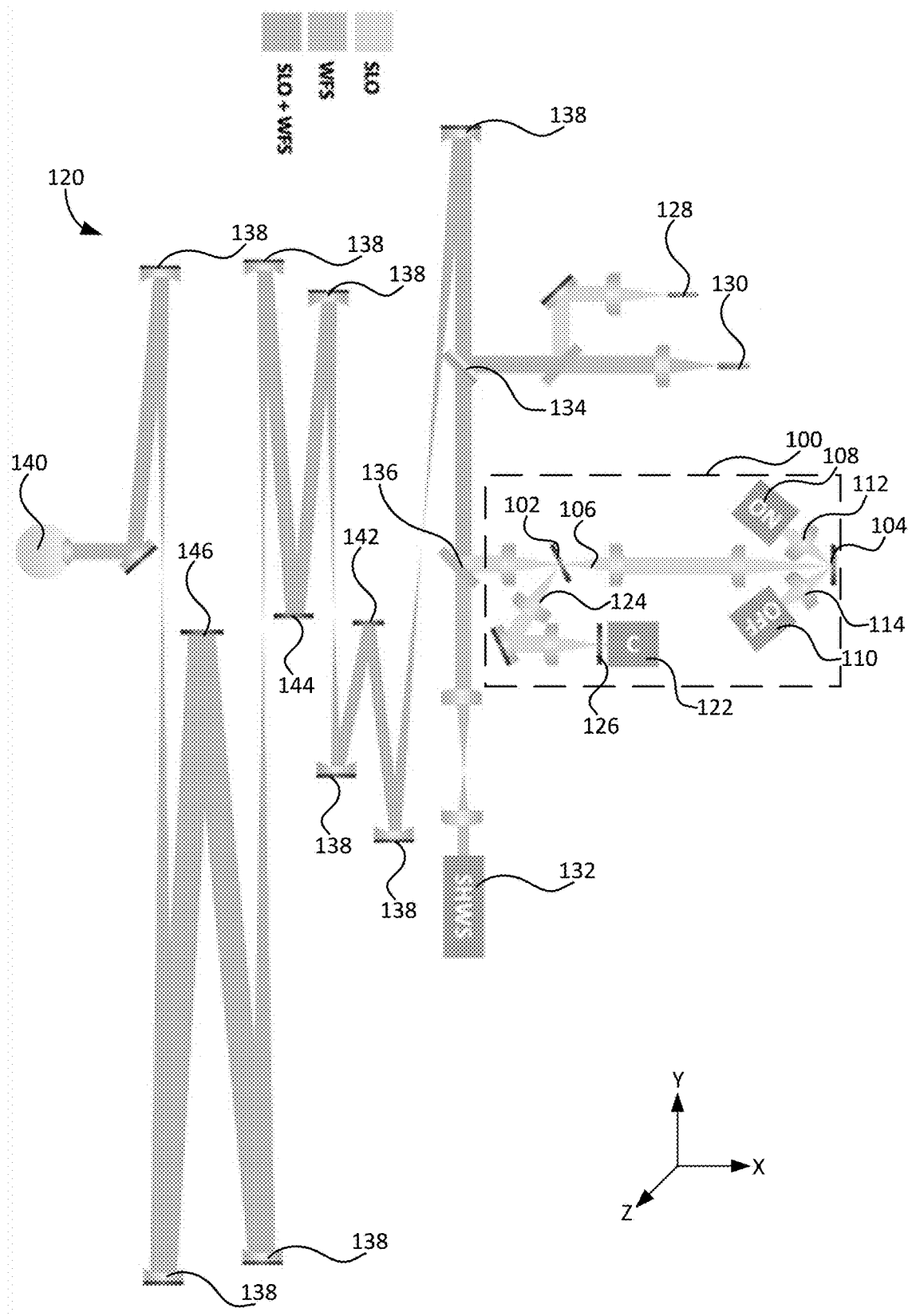
FIG. 1B illustrates an example DCAOSLO system incorporating a multi-channel device as described with respect to FIG. 1A.

FIG. 1B illustrates an example DCAOSLO system incorporating a multi-channel device as described with respect to FIG. 1A. Referring to FIG. 1B, an example DCAOSLO system 120 incorporating a multi-channel device includes a light source 128 of the light for imaging, a wavefront sensing beacon 130 arranged to provide additional light (e.g., to measure a wavefront from the object 140 using a wavefront sensor 132), a wavefront sensor 132 arranged to receive the light, a dichroic/beam splitter 134 arranged to combine light from the light source 128 with the additional light from the wavefront sensing beacon 130, a dichroic/beam splitter 136 arranged to reflect the light to the reflective mask 102 and to transmit the additional light from wavefront sensing beacon 130 and positioned between the dichroic/beam splitter 134 and the wavefront sensor 132, four concave spherical mirror telescopes 138 arranged in a non-planar folding configuration and positioned between the beam splitter 134 and an object 140 to be imaged, a horizontal scanner 142, a vertical scanner 144, and a deformable mirror 146 positioned within the four concave spherical mirror telescopes 138.

In some cases, the system 120 further includes a system controller and memory storing instructions that when executed by the system controller, direct the system 120 to adjust the horizontal scanner 142, the vertical scanner 144, and the deformable mirror 146 positioned within the four concave spherical mirror telescopes 138 to image the object 140. In some cases, the object 140 is an eye.

A specific embodiment implementation of a DCAOSLO system 120 includes four concave spherical mirror telescopes arranged in a non-planar folding configuration to minimize astigmatism, a 796 nm superluminescent diode (S-790-I-15-M, Superlum) as a point source for imaging (e.g., light source 128), an 852 nm laser diode (LP852-SF30, Thorlabs) as a wavefront sensing beacon (e.g., wavefront sensing beacon 130). With a fast-axis resonant scanner (e.g., horizontal scanner 142) running at 15.3 kHz and 599 lines per frame, images can be acquired at –26 Hz over 1.2° square field-of-view. Ocular monochromatic aberrations can be measured using a custom Shack-Hartmann wavefront sensor (e.g., wavefront sensor 132) and corrected by a 97-actuator deformable mirror (DM97, ALPAO) at –9 Hz (e.g., deformable mirror 146).

In this example implementation, the multi-channel device 100 can provide a 796 nm collection channel with a custom reflective elliptical annular mask (e.g., reflective mask 102) positioned at –50 degrees in a de-scanned retinal conjugate plane to reflect the central circular 2 airy disk diameter (ADD) of focal spot into the confocal channel and transmit 2-20 ADD into the non-confocal channel. The 2 ADD confocal light can be further filtered by a 0.6 ADD pinhole (e.g., pinhole 126) before reaching an image detector (e.g., third light detector 122) for sub-Airy disk confocal detection. The 2-20 ADD non-confocal portion of light can be relayed onto a 1920×1080 DMD (DLP6500FYE, Texas Instruments) (e.g., DMD 104) positioned in a second (retinal) conjugate plane. The DMD can be rotated ~45 degrees around an optical axis to keep the incoming light and outgoing lights in the same horizontal plane, parallel to the optical table. Two light detectors, an ON image detector (e.g., ON image detector 108) and an OFF image detector (e.g., OFF image detector 110), can be used to record multiplexed light intensity from ON-mirrors and OFF mirrors, respectively. A lens can be positioned before each detector (e.g., ON lens 112 and OFF lens 114) to collect diffracted light.

In some cases, confocal and non-confocal paths may be switched by using a reflective pinhole mask instead of an elliptical mask and change the magnification between the mask and the DMD to perform compressed sensing on confocal light instead for the pixel reassignment task. As mentioned above, although FIG. 1B shows an AOSLO implementation, it should be understood that the described multi-channel device can be implemented in other imaging systems that require multi-channel light detection in a scanning microscope.

Figure 2:
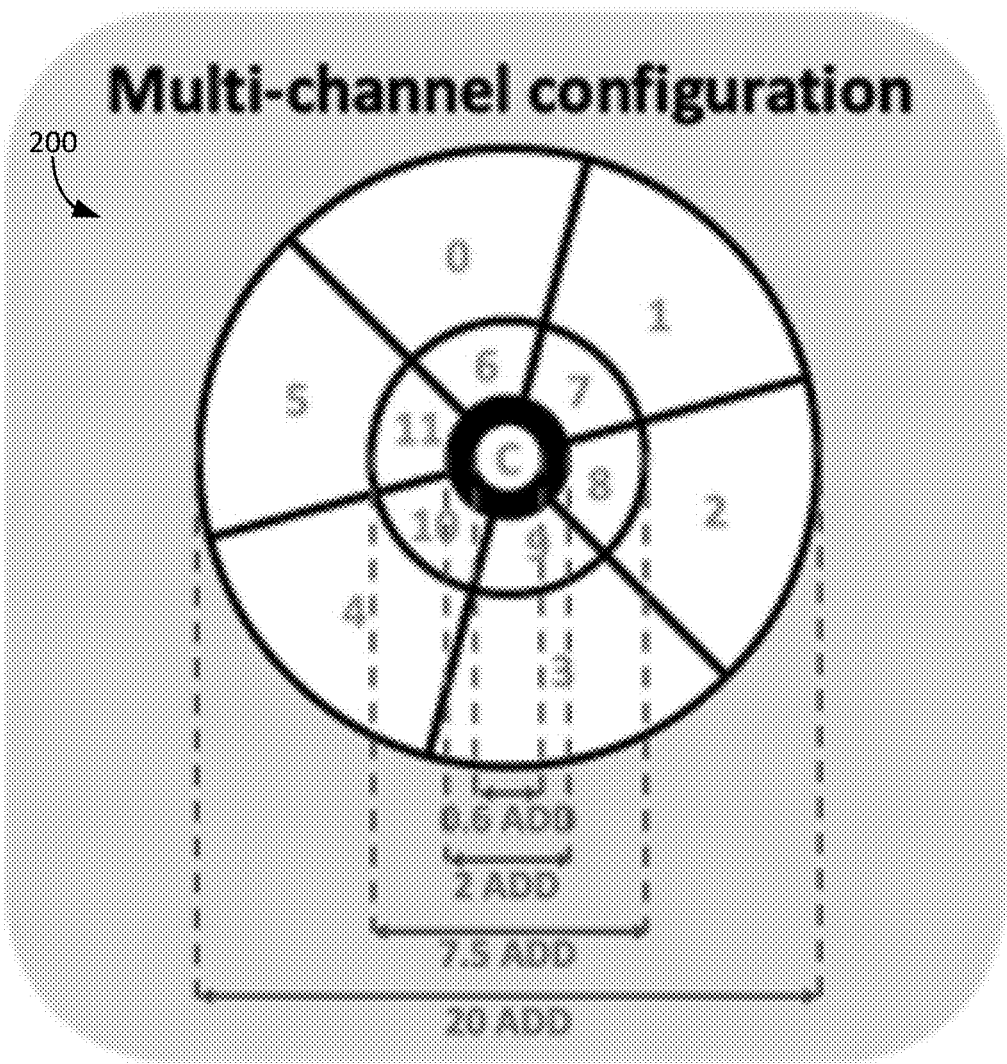
FIG. 2 illustrates a multi-channel detection configuration.

FIG. 2 illustrates a multi-channel detection configuration. Referring to FIG. 2, a multi-channel detection configuration 200 is divided into 13 distinct sections. The 13 distinct sections include 12 sections that receive non-confocal channels of light (e.g., labeled 0-11) and 1 section that receives a confocal channel of light (e.g., labeled "C"). For non-confocal channels 0-11, each section includes micromirrors that rotate together between an ON state and an OFF state according to a pre-stored DMD pattern sequence. Accordingly, each section receives light from a different non-confocal channel or a confocal channel; and light that is transmitted to each section is further reflected by that section's micromirrors to an ON image detector or an OFF image detector (e.g., as described with respect to FIGS. 1A and 1B). Although the detection configuration with 13 distinct sections are illustrated in FIG. 2, it should be understood that any number/geometry of distinct sections for use in a DMD pattern sequence may be used.

In a specific embodiment, random DMD patterns can be designed to compressively sample 12 detection channels of non-confocal light up to 20 ADD. Such DMD patterns can be created by dividing the central portion of DMD pixels (d=20 ADD) into 6 sectors, each of which can be further divided into two by a smaller concentric ring (d=7.5 ADD), resulting in 12 distinct sections. DMD pixels in each channel can be modulated together, forming a "super-pixel." DMD pixels that lie outside of the channels can display a stripe pattern to equally distribute background light into the ON image detector and the OFF image detector.

Figure 3:
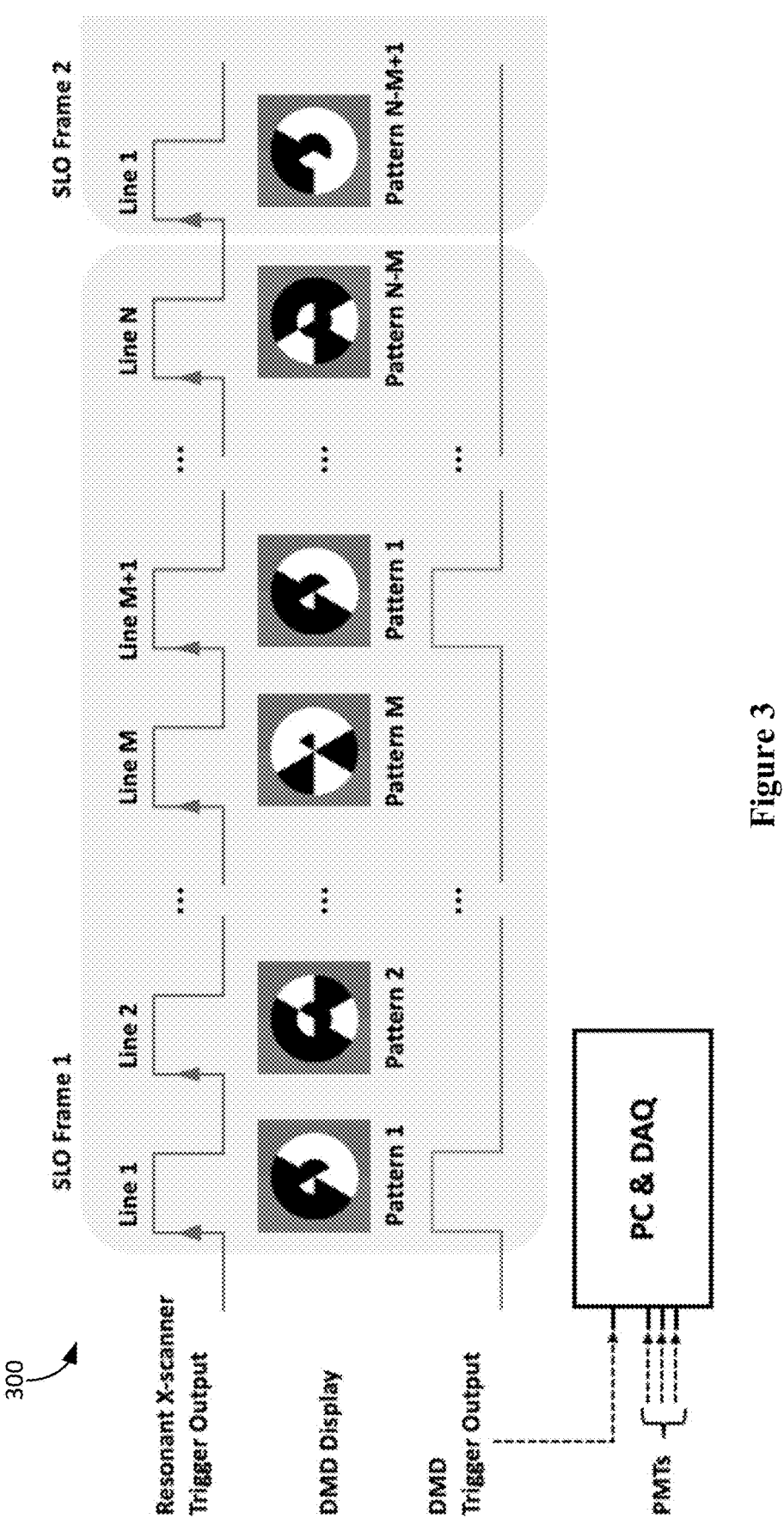
FIG. 3 illustrates a multi-channel DMD operation.

FIG. 3 illustrates a multi-channel DMD operation. Referring to FIG. 3, a multi-channel DMD operation 300 includes a number of DMD patterns that are prestored into on-board memory of a DMD. The DMD may be operated, for example, at an imaging raster line of 15.3 kHz. The DMD patterns are used to create a DMD pattern sequence that is 512 patterns long (e.g., M=512). During imaging, the pre-stored DMD pattern sequence is repeatedly cycled through (e.g., via a DMD controller) and is triggered by TTL pulses generated from a resonant scanner (e.g., horizontal scanner 142 of FIG. 1B) at the start of each raster line. The number of patterns that can be saved, the length of pattern sequences, and how fast the DMD patterns can be modulated may differ based on the model of the DMD and its on-board controller.

As an example, with lines per frame set to 599 (e.g., N=599), continuous acquisition of 512 distinct compressed sensing measurement frames is attained or a fixed field-of-view on a stationary object. In some cases, the first pattern sequence (e.g., first cycle) of the pre-stored DMD pattern sequence is tagged for identification with a trigger output synchronously with other channels used for the imaging detectors (e.g., ON image detector 108 and OFF image detector 110 of FIGS. 1A and 1B). This tagging may be recorded on a separate channel on a digitizer and allows for the accurate identification of the DMD pattern sequence used for each sample measurement. In some cases, the DMD controller directs the DMD to perform this tagging.

FIG. 4A illustrates a flow diagram of a method of creating a reconstruction image from image data collected using a multi-channel device as described herein. Referring to FIG. 4A, the method 400 includes receiving (402) ON pattern image data of an object and OFF pattern image data of the object. The ON pattern image data is captured by an ON image detector that receives light from micromirrors of a digital micromirror device (DMD) that are rotated to an ON state according to a pre-stored DMD pattern sequence and the OFF pattern image data is captured by an OFF image detector that receives light from micromirrors of the DMD that are rotated to an OFF state according to the pre-stored DMD pattern sequence (e.g., as described above with respect to FIGS. 1A-3).

For example, at each scan point (x', y'), the intensity distribution of returning light X (x', y', c) is coded by the binary DMD pattern being displayed, M (x', y', c) and its complementary pattern, 1-M (x', y', c), resulting in two measurement values, YON(x', y') and YOFF(x', y').

The method 400 further includes determining (404) a DMD difference between the ON pattern image data and the OFF pattern image data. For example, after 2D scanning, a 2-D DCAOSLO measurement frame Y (x, y) is obtained by subtracting YOFF(x, y) from YON(x, y), which removes background signal while retaining the encoding of the light distribution of C channel images X (x, y, c). Mathematically, this measurement can be expressed as:

$$Y(x, y) = Y_{ON}(x, y) - Y_{OFF}(x, y) = \sum_{c=1}^{C} (2M(x, y, c) - 1) \cdot X(x, y, c) \quad (1)$$

$$Y_{ON}(x, y) = \sum_{c=1}^{C} M(x, y, c) \cdot X(x, y, c) \quad (2)$$

$$Y_{OFF}(x, y) = \sum_{c=1}^{C} (1 - M(x, y, c)) \cdot X(x, y, c) \quad (3)$$

Next, the complete DCAOSLO forward model is defined by the sensing matrix $A_{DCAOSLO}$:

$$y = A_{DCAOSLO}x \quad (4)$$

where y=vec(Y) and x=vec(X).

The method 400 further includes performing (406) image reconstruction for the object based on the DMD difference. FIG. 4B illustrates a flow diagram of a method of performing image reconstruction that can be used as part of the method of creating a reconstruction image. Referring to FIG. 4B, a method 420 of performing (e.g., step 406 of FIG. 4A) image reconstruction includes generating (422) an artificial image, converting (424) the artificial image to pseudo ON pattern image data and pseudo OFF pattern image data, determining (426) a pseudo DMD difference between the pseudo ON pattern image data and the pseudo OFF pattern image data, and determining (428) a loss difference between the DMD difference and the pseudo DMD difference.

In some cases, the method 420 further includes summing the ON pattern image data and the OFF pattern image data. In some cases, a set of inputs for generating (422) an artificial image includes the sum of the ON image data and the OFF image data.

Referring back to FIG. 4A, the method 400 further includes updating (408) weights (e.g., of the machine learning model/reconstruction network) for generating the artificial image, and repeating (410) the performing (406) and updating (408) steps until the loss difference between the DMD difference and the pseudo DMD difference reaches a minimum threshold.

As a mathematical example, to generate (422) an artificial image x from measurement y, a machine learning model (e.g., an untrained, deep generative convolution neural network) is used as an implicit image prior. Instead of directly updating x during reconstruction, x is optimized as an output of the machine learning model GO(z) from a fixed input z by updating (408) the machine learning model's randomly initialized weights 0 via backpropagation. The optimal network weights θ* can be obtained by minimizing a loss function L that incorporates empirical information that is application specific using an optimizer, such as, for example, a gradient descent:

$$\theta^* = \text{argmin}_\theta L(G_\theta(z), A_{DCAOSLO}, y) \quad (5)$$

In some cases, updating (408) the network weights 0 for generating (422) the artificial image includes minimizing a mean squared error for the determined (428) loss difference between the DMD difference and the pseudo DMD difference. In some cases, the method 400 further includes displaying a final artificial image upon reaching the minimum threshold.

In some cases, early stopping is employed to prevent the machine learning model from overfitting to noise. After network optimization, (e.g., the reaching of a minimum threshold), the generated image(s) x can be defined as the network output with input z:

$$x = G_\theta \cdot (z) \quad (6)$$

Figure 5A:
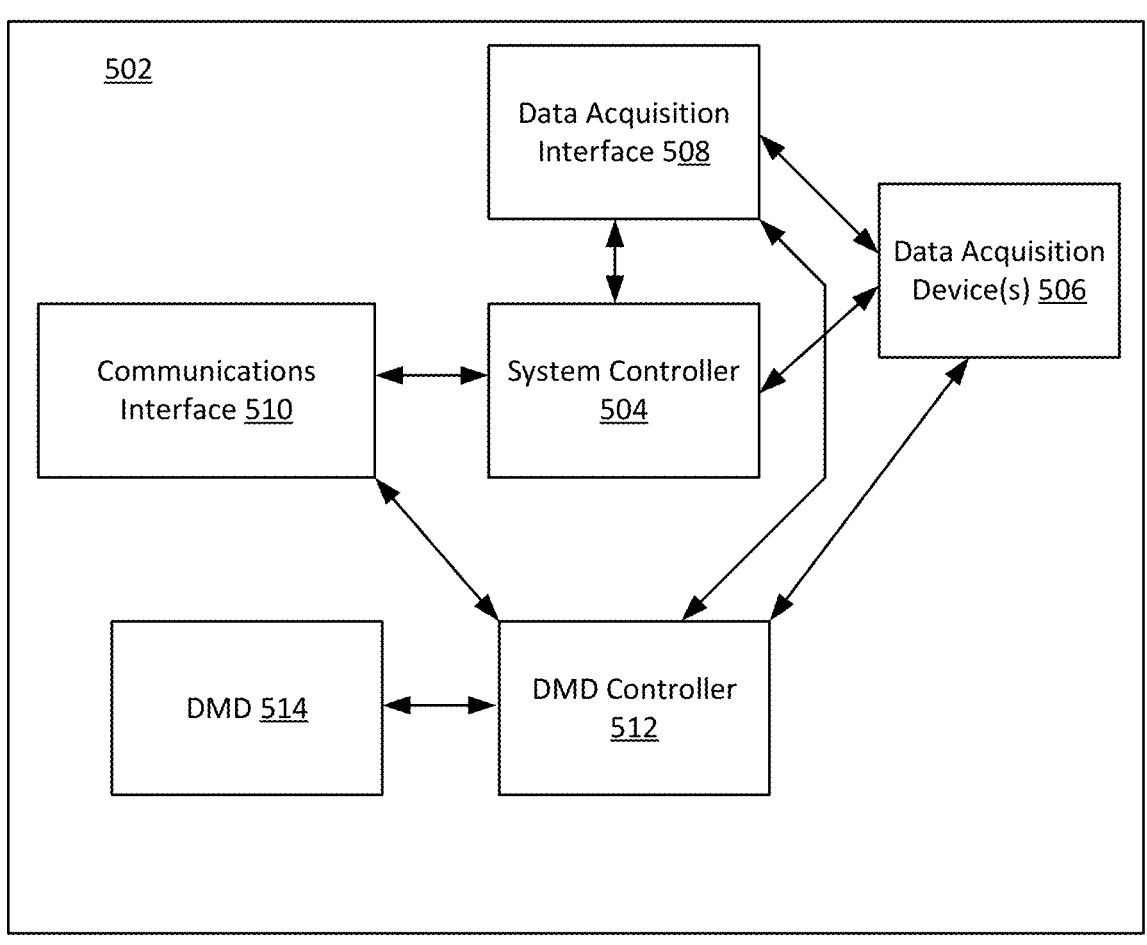
FIG. 5A illustrates a block diagram of an imaging system.

FIG. 5A is a block diagram of an imaging system. Referring to FIG. 5A, an imaging system 502 (e.g., DCAO-SLO system 120) can include a system controller 504 coupled to one or more data acquisition devices 506 (e.g., image/light detectors, scanners, beam splitter(s), wavefront sensing beacon(s), wavefront sensor(s), dichroic(s), telescopes, light sources, and/or a DMD) that are used to capture/acquire a plurality of images/image data of an object via a data acquisition interface 508. In some cases, the system controller 504 can include or be coupled to a communications interface 510 for communicating with another computing system, for example computing system 520 of FIG. 5B.

The DCAOSLO system 502 can further include a DMD controller 512 coupled to a DMD 514 to control the state of the micromirrors (e.g., ON state and OFF state). In some cases, the DMD controller 512 can be coupled to one or more data acquisition devices 506 (e.g., ON image detector 108 and OFF image detector 110) that are used to capture/acquire a plurality of images/image data of an object via the data acquisition interface 508. In some cases, the DMD controller 512 can include or be coupled to the communications interface 510 for communicating with another computing system, for example computing system 520 of FIG. 5B. In some cases, the system controller 504 and the DMD controller 512 are a single controller.

System controller 504 and/or DMD controller 512 can include one or more processors with corresponding storage having instructions for execution and/or control logic for controlling the data acquisition devices 506 and/or DMD 514 to acquire a plurality of images/image data of an object taken and can include memory storage for storing said image data. Images/image data captured by the one or more data acquisition devices 506 can be processed (e.g., pre-processing operations for supporting data transmission and/or reconstruction) at the system controller 504 and/or DMD controller 512 before being communicated/sent to another computing device via the communications interface 510. In some cases, the imaging system incorporates components/features of the computing system 520 described with respect to FIG. 5B.

Figure 5B:
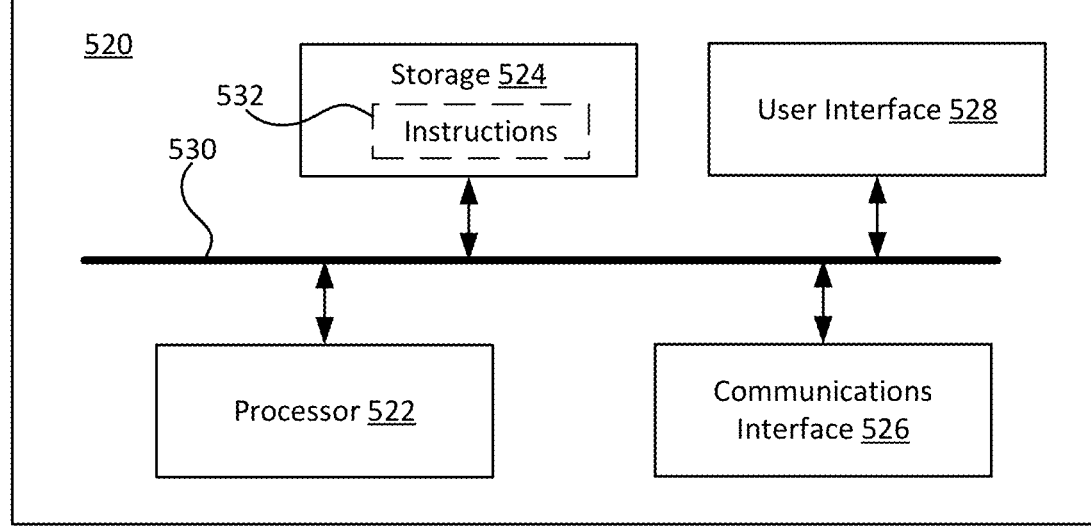
FIG. 5B illustrates a computing system that can be used for image reconstruction for a DCAOSLO system.

FIG. 5B illustrates a computing system that can be used for image reconstruction for a DCAOSLO system. Referring to FIG. 5B, a computing system 520 can include a processor 522, storage 524, a communications interface 526, and a user interface 528 coupled, for example, via a system bus 530. Processor 522 can include one or more of any suitable processing devices ("processors"), such as a microprocessor, central processing unit (CPU), graphics processing unit (GPU), field programmable gate arrays (FPGAs), application-specific integrated circuits (ASICs), logic circuits, state machines, application-specific standard products (ASSPs), system-on-a-chip systems (SOCs), complex programmable logic devices (CPLDs), etc. Storage 524 can include any suitable storage media that can store instructions 532 for performing DCAOSLO image reconstruction, such as for example, method 400 and/or method 420. Suitable storage media for storage 524 includes random access memory, read only memory, magnetic disks, optical disks, CDs, DVDs, flash memory, magnetic cassettes, magnetic tape, magnetic disk storage or other magnetic storage devices, or any other suitable storage media. As used herein, "storage," "memory storage," and "storage media" do not consist of transitory, propagating waves. Instead, these terms refer to non-transitory media.

Communications interface 526 can include wired or wireless interfaces for communicating with an imaging system 502 such as described with respect to FIG. 5A, as well as interfaces for communicating with the "outside world" (e.g., external networks). User interface 528 can include a display on which the enhanced resolution images can be displayed as well as suitable input device interfaces for receiving user input (e.g., mouse, keyboard, microphone).

Figure 6:
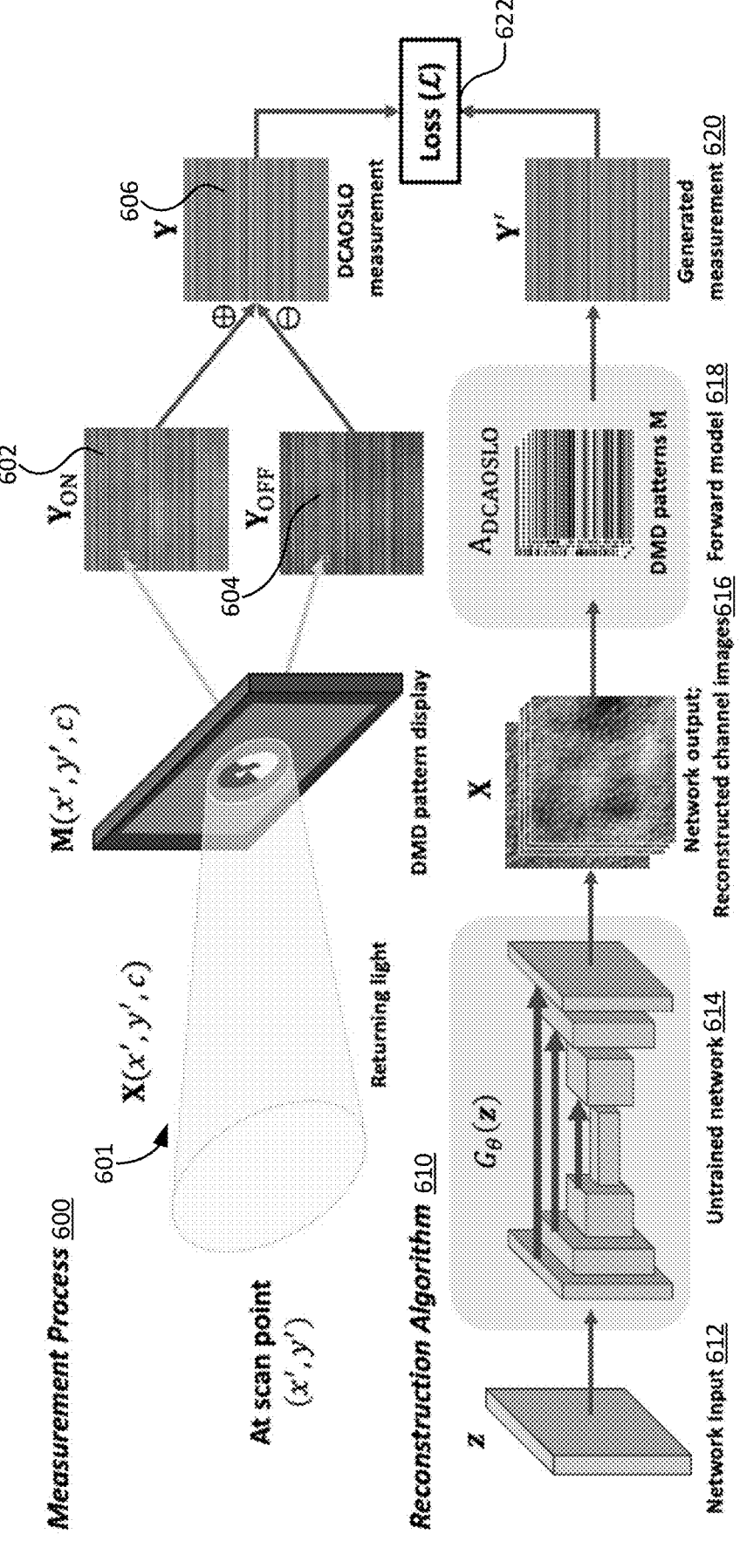
FIG. 6 illustrates a specific embodiment of a method of creating a reconstruction image from data collected using a multi-channel device as described herein.

FIG. 6 illustrates a specific embodiment of a method of creating a reconstruction image from data collected using a multi-channel device as described herein. Referring to FIG. 6, a measurement process 600 includes a DCAOSLO system 601 (e.g., a system incorporating a multi-channel device 100) that captures image data (e.g., for each scan point x', y') that includes ON pattern image data 602 and OFF pattern image data 604. Next, a DMD difference (e.g., DCAOSLO measurement 606) between the ON pattern image data 602 and the OFF pattern image data 604 is determined. Next, a reconstruction algorithm 610 is utilized. For the reconstruction algorithm 610, a network input 612 is inputted into an untrained network 614. In some cases, the network input 612 includes random noise. In some cases, the network input 612 includes a sum of the ON pattern image data 602 and the OFF pattern image data 604.

The untrained network 614 generates an artificial image (e.g., reconstructed channel images 616) based on the network input 612 and/or weights of the machine learning model/reconstruction network. The reconstructed channel images 616 are then converted into pseudo ON pattern image data and pseudo OFF pattern image data in a forward model 618. The forward model then determines a pseudo DMD difference between the pseudo ON pattern image data and the pseudo OFF pattern image data as a generated measurement 620.

A loss difference (L) 622 is determined between the DMD difference and the pseudo DMD difference. The weights (e.g., of the untrained network 614 for generating the artificial image are also updated. If the loss difference (L) 622 meets a minimum threshold, the reconstructed channel images 616 are an output of the reconstruction algorithm and may be subsequently displayed and/or stored. Alternatively, if the loss difference (L) 622 does not meet a minimum threshold, the reconstruction algorithm 610 is iteratively utilized until the loss difference (L) meets a minimum threshold. In some cases, the weights of the untrained network 614 are only updated if the loss difference (L) 622 does not meet the minimum threshold.

Figure 7:
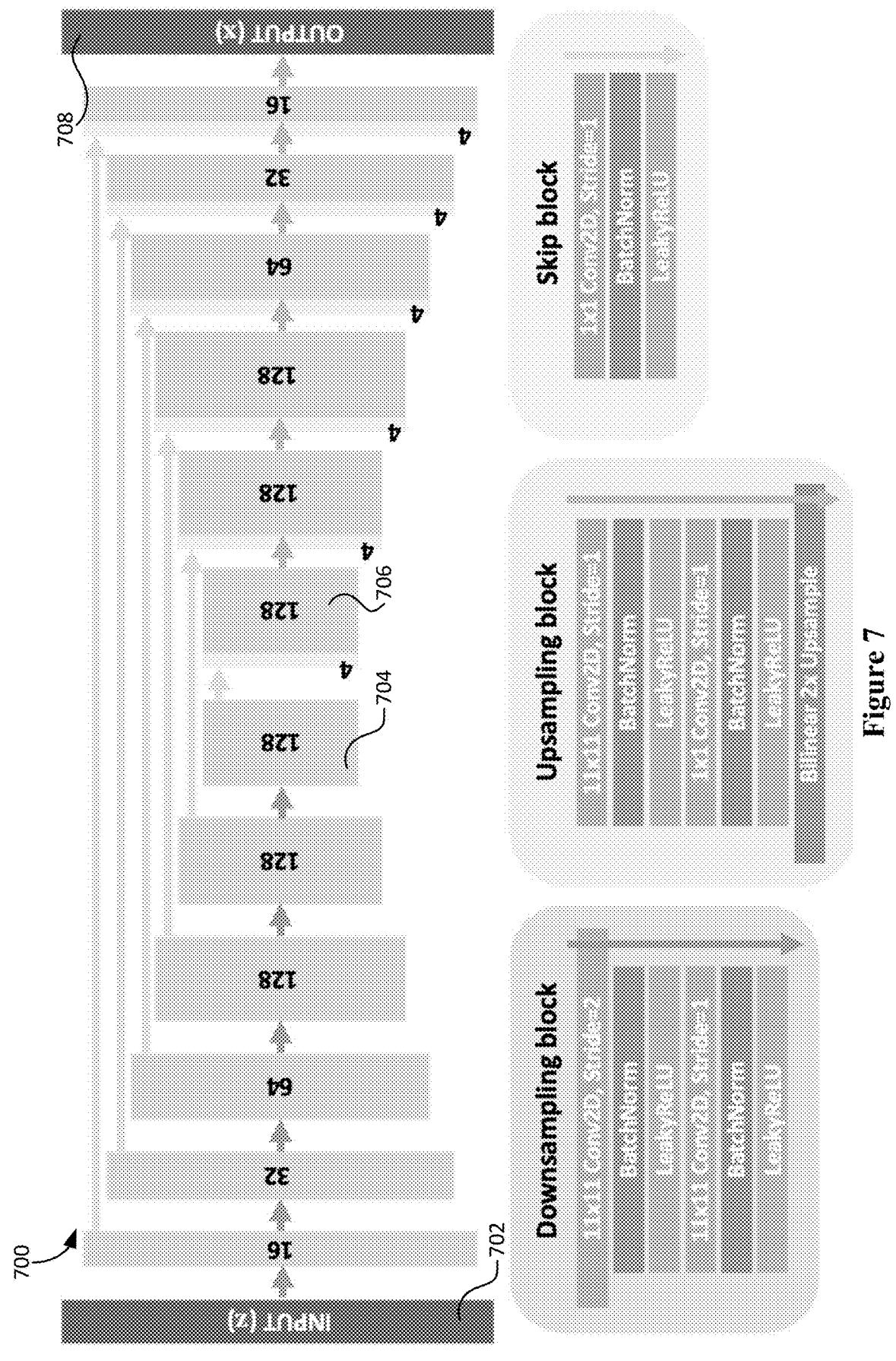
FIG. 7 illustrates a specific embodiment of network architecture used to create a reconstruction image.

FIG. 7 illustrates a specific embodiment of network architecture used to create a reconstruction image. Referring to FIG. 7, a network architecture 700 used to create a reconstruction image utilizes multiple DCAOSLO measurements. Numbers in the figure indicate the numbers of feature maps at each respective layer. From the input 702 to the left middle block 704, downsampling operations are performed. From the right middle block 706 to the output 708, upsampling operations are performed. Skip connections from each equivalently numbered block in the downsampling operations and the upsampling operations are also utilized.

In detail, to correct for eye motion, DCAOSLO measurements can be co-registered using confocal image registration parameters that are calculated using a strip-based normalized cross-correlation image registration algorithm. Channel images x can be reconstructed using a convolution neural network with U-net-like architecture with skip connections. Downsampling can be performed using strided convolution with stride=2. Upsampling can be performed using bilinear upsampling. A sigmoid operation can be applied at the last layer of the convolution neural network to ensure values of x are between 0 and 1.

In a specific example, 1024 copies of averaged darkfield images were created by summing ON image data and OFF image data as a fixed input z to the convolution neural network. An optimal network weight θ* was found by minimizing the mean squared error loss between generated measurements y' and DCAOSLO measurements y (e.g., loss difference (L) 622 of FIG. 6):

$$\theta^* = \mathrm{argmin}_\theta \| y - A_{DCAOSLO} G_\theta(z) \| \tag{7}$$

Experimental Results

The inventors used an embodiment of the DCAOSLO system as provided above to image the retina of 6 healthy adult volunteers with no signs of ocular disease according to their medical history. Prior to imaging, dilation was performed by administration of a solution of 0.5% tropicamide and 5% phenylephrine.

The inventors compared the DCAOSLO reconstructions (e.g., final artificial images that reached a minimum threshold) with non-confocal channel images acquired using conventional multi-offset aperture AOSLO imaging. Imaging was performed by turning on one of the DMD super-pixels for the duration of an SLO frame acquisition, with the subject fixated on the same target as that of DCAOSLO acquisition. A 12-pattern long sequence that contained 12 offset aperture patterns was generated and this pattern sequence was repeatedly cycled through by TTL pulses generated from the acquisition software at the start of each SLO frame. Prior to averaging, eye motion in channel images were corrected using their confocal image registration parameters.

Figures 8, 9:
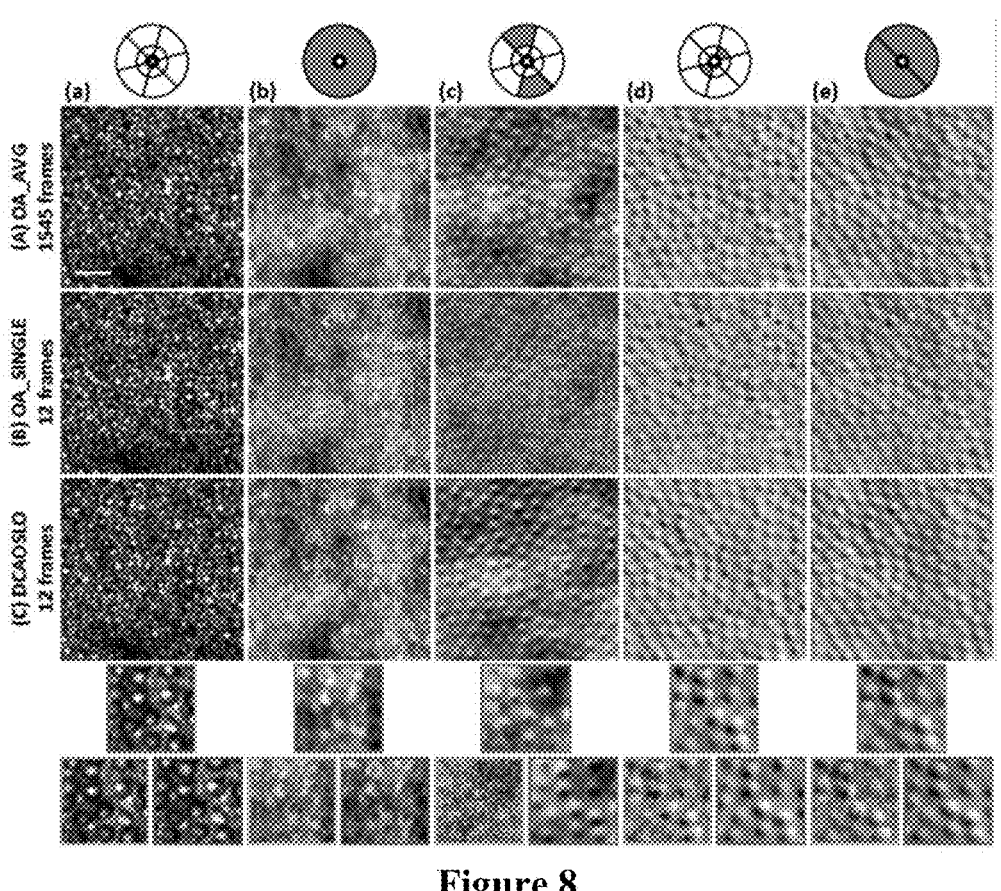
FIGS. 8-10 illustrate comparison images from known AOSLO systems and the DCAOSLO systems provided herein.
Figure 10:
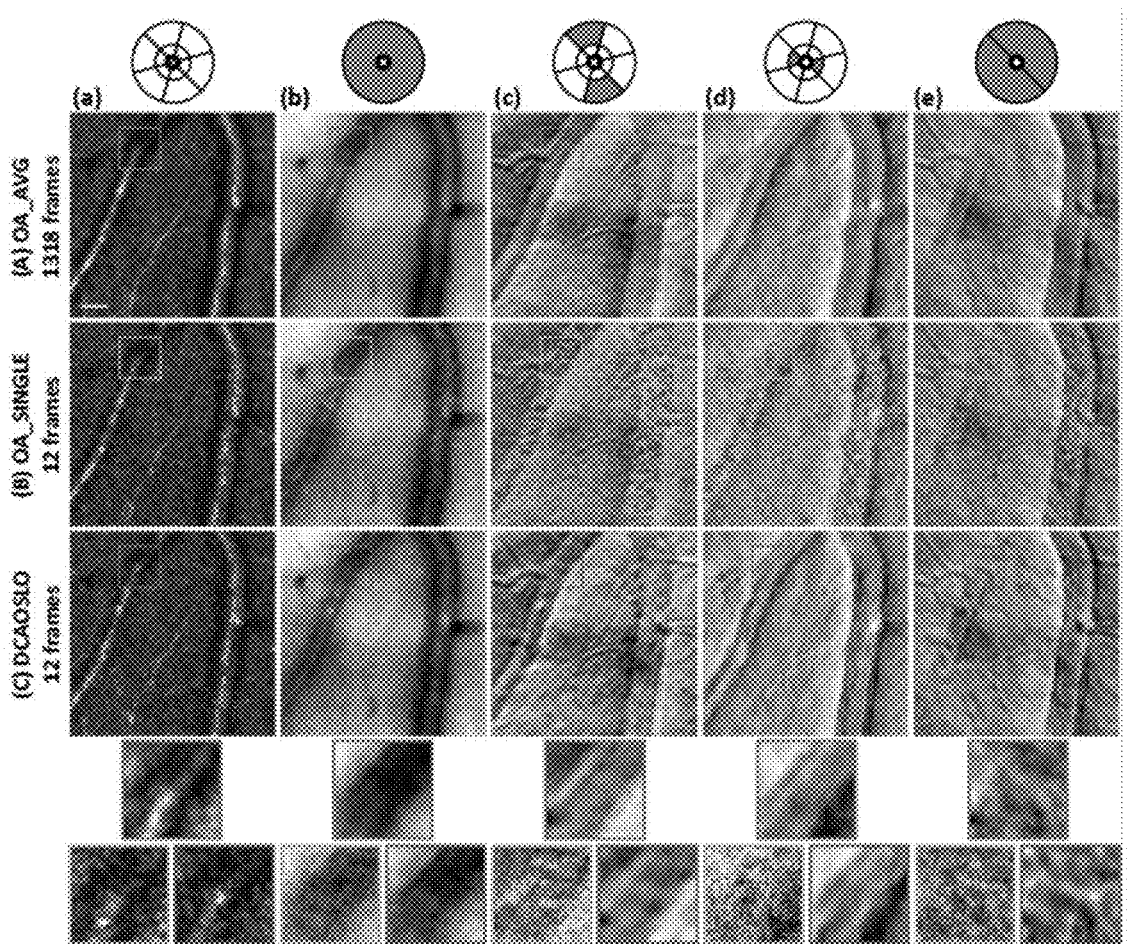

FIGS. 8-10 illustrate comparison images from known AOSLO systems and the DCAOSLO systems provided herein. Referring to FIG. 8, images of a photoreceptor layer of an eye can be seen. Specifically, Row A illustrates images generated using a total of 1,545 AOSLO frames, which allowed for 124-133 frames to be averaged per non-confocal channel. Row B illustrates images generated using a total of 12 AOSLO frames, which only allowed for a single frame per channel. Row C illustrates images generated using a total of 12 DCAOSLO measurements (e.g., as described above). This represents a reduction in imaging time of ~129 times versus the images illustrated in Row A and the same imaging time versus the images illustrated in Row B.

Referring to FIG. 9, images of a photoreceptor layer of an eye can be seen. Specifically, Row A illustrates images generated using a total of 798 AOSLO frames, which allowed for 61-72 frames to be averaged per channel. Row B illustrates images generated using a total of 12 AOSLO frames, which only allowed for a single frame per channel. Row C illustrates images generated using a total of 12 DCAOSLO measurements (e.g., as described above). This represents a reduction in imaging time of ~167 times versus the images illustrated in Row A and the same imaging time versus the images illustrated in Row B.

Referring to FIGS. 8 and 9, similar quality confocal images of Row B, Column A and Row C, Column A indicate similar imaging conditions of AOSLO imaging and DCAO-SLO imaging. The darkfield image of DCAOSLO (Row C, Column B) was generated by averaging summed ON image data and OFF image data without the need for compressed sensing reconstruction, which was also used as the input to a reconstruction network. This is an advantage of DCAO-SLO over AOSLO imaging, in which all the individual channel images with low signal-to-noise ratio (SNR) must be acquired and then summed to generate a darkfield image. Channel image reconstructions of DCAOSLO (Row C, Columns C-E) demonstrate great SNR improvement over the images using an AOSLO single frame per image (Row B, Columns C-E), revealing the photoreceptor structure while capturing intensity variations around individual cells that are associated with radial position of channels.

Referring to FIG. 10, images of a nerve fiber layer of an eye can be seen. Specifically, Row A illustrates images generated using a total of 1318 AOSLO frames, which allowed for 101-117 frames to be averaged per channel. Row B illustrates images generated using a total of 12 AOSLO frames, which only allowed for a single frame per channel. Row C illustrates images generated using a total of 12 DCAOSLO measurements (e.g., as described above). This represents a reduction in imaging time of ~110 times versus the images illustrated in Row A and the same imaging time versus the images illustrated in Row B. As can be seen, channel reconstruction images of DCAOSLO (Row C, Col-umns C-E) were able to reveal both small and large vessels, well delineating the vessel wall structures that were hidden in the images using an AOSLO single frame per image (Row B, Columns C-E) due to low SNR.

Additionally, the inventors discovered that fast multi-channel detection by DCAOSLO allows for monitoring of dynamic retinal features in these channels such as blood flow using time-series compressed sensing measurement.

Additionally through stitching of multiple smaller field-of-view compressed sensing measurements acquired at differ-ent locations on the object (e.g., retina), fast wide field-of-view multi-channel imaging is achievable.

Although the subject matter has been described in lan-guage specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A system comprising:

a reflective mask positioned in a first plane;

a digital micromirror device (DMD) that is positioned in a second plane to receive transmitted light from the reflective mask via a non-confocal channel, the DMD comprising:

micromirrors that rotate between an ON state and an OFF state;

a DMD controller; and memory storing instructions that when executed by the DMD controller, direct the DMD to rotate the micro-mirrors between the ON state and the OFF according to a pre-stored DMD pattern sequence during imag-ing;

an ON image detector that captures ON image data of the transmitted light directed by the micromirrors in the ON state;

an OFF image detector that captures OFF image data of the transmitted light directed by the micromirrors in the OFF state; and a first storage storing instructions that when executed by a computing system, direct the computing system to:

receive ON pattern image data of an object and OFF pattern image data of the object, wherein the ON pattern image data is captured by the ON image detector that receives light from micromirrors of the DMD that are rotated to the ON state according to the pre-stored DMD pattern sequence and wherein the OFF pattern image data is captured by the OFF image detector that receives light from micromirrors of the DMD that are rotated to the OFF state accord-ing to the pre-stored DMD pattern sequence;

determine a DMD difference between the ON pattern image data and the OFF pattern image data;

perform image reconstruction for the object based on the DMD difference, wherein the image reconstruc-tion comprises:

generating an artificial image;

converting the artificial image to pseudo ON pattern image data and pseudo OFF pattern image data;

determining a pseudo DMD difference between the pseudo ON pattern image data and the pseudo OFF pattern image data; and determining a loss difference between the DMD difference and the pseudo DMD difference;

update weights for generating the artificial image; and repeat the performing and updating steps until the loss difference between the DMD difference and the pseudo DMD difference reaches a minimum thresh-old.

2. The system of claim 1, wherein the non-confocal channel is a plurality of non-confocal channels, wherein the micromirrors of the DMD are divided into distinct sections corresponding to the pre-stored DMD pattern sequence, wherein the DMD is further positioned to receive the transmitted light from the reflective mask via a confocal channel, and wherein each distinct section receives the transmitted light from a different non-confocal channel or the confocal channel.

3. The system of claim 1, wherein the instructions executed by the DMD controller further direct the DMD to repeatedly cycle through the pre-stored DMD pattern sequence in response to TTL pulses generated from a horizontal scanner.

4. The system of claim 3, wherein the instructions executed by the DMD controller further direct the DMD to tag a first cycle of the pre-stored DMD pattern sequence for identification.

5. The system of claim 1, wherein the ON state is +12 degrees relative to the second plane and the OFF state is −12 degrees relative to the second plane.

6. The system of claim 1, further comprising:

an ON lens positioned between the DMD and the ON image detector; and an OFF lens positioned between the DMD and the OFF image detector.

7. The system of claim 1, wherein the ON image detector and the OFF image detector are photomultiplier tubes.

8. The system of claim 1, wherein the ON image detector and the OFF image detector are avalanche photodiodes.

9. The system of claim 1, wherein the reflective mask is a reflective elliptical annular mask.

10. The system of claim 1, wherein the reflective mask is a reflective pinhole mask.

11. The system of claim 1, further comprising:

a third light detector that captures confocal image data from reflected light that is reflected from the reflective mask via a confocal channel; and a pinhole positioned between the third light detector and the reflective mask.

12. The system of claim 10, further comprising:

a light source of the light for imaging;

a wavefront sensing beacon arranged to provide additional light;

a wavefront sensor arranged to receive the light;

a first dichroic arranged to combine light from the light source with the additional light from the wavefront sensing beacon;

a second dichroic arranged to reflect the light to the reflective mask and to transmit the additional light from the wavefront sensing beacon and positioned between the first dichroic and the wavefront sensor;

four concave spherical mirror telescopes arranged in a non-planar folding configuration and positioned between the beam splitter and an object to be imaged; and a horizontal scanner, a vertical scanner, and a deformable mirror positioned within the four concave spherical mirror telescopes.

13. The system of claim 12, further comprising a system controller and a second memory storing instructions that when executed by the system controller, direct the system to adjust the horizontal scanner, the vertical scanner, and the deformable mirror positioned within the four concave spherical mirror telescopes to image the object.

14. A computer-implemented method comprising:

receiving ON pattern image data of an object and OFF pattern image data of the object, wherein the ON pattern image data is captured by an ON image detector that receives light from micromirrors of a digital micromirror device (DMD) that are rotated to an ON state according to a pre-stored DMD pattern sequence and wherein the OFF pattern image data is captured by an OFF image detector that receives light from micromirrors of the DMD that are rotated to an OFF state according to the pre-stored DMD pattern sequence;

determining a DMD difference between the ON pattern image data and the OFF pattern image data;

performing image reconstruction for the object based on the DMD difference, wherein the image reconstruction comprises:

generating an artificial image;

converting the artificial image to pseudo ON pattern image data and pseudo OFF pattern image data;

determining a pseudo DMD difference between the pseudo ON pattern image data and the pseudo OFF pattern image data; and determining a loss difference between the DMD difference and the pseudo DMD difference;

updating weights for generating the artificial image; and repeating the performing and updating steps until the loss difference between the DMD difference and the pseudo DMD difference reaches a minimum threshold.

15. The method of claim 14, wherein the micromirrors of the DMD are divided into distinct sections corresponding to the pre-stored DMD pattern sequence, wherein each distinct section receives the light from a different non-confocal channel or a confocal channel.

16. The method of claim 14, further comprising summing the ON pattern image data and the OFF pattern image data, wherein an initial set of the inputs for generating the artificial image comprises the sum of the ON image data and the OFF image data.

17. The method of claim 14, wherein a machine learning model performs the step of generating the artificial image.

18. The method of claim 14, wherein updating the weights for generating the artificial image comprises minimizing a mean squared error for the determined loss difference between the DMD difference and the pseudo DMD difference.

19. The method of claim 14, further comprising displaying a final artificial image upon reaching the minimum threshold.

* * * * *